United States Patent
Schulze-Ganzlin

(10) Patent No.: US 7,815,371 B2
(45) Date of Patent: Oct. 19, 2010

(54) X-RAY EMITTER

(75) Inventor: Ulrich Schulze-Ganzlin, Lorsch (DE)

(73) Assignee: Sirona Dental Systems GmbH, Bensheim (DE)

( * ) Notice: Subject to any disclaimer, the term of this patent is extended or adjusted under 35 U.S.C. 154(b) by 33 days.

(21) Appl. No.: 12/261,246

(22) Filed: Oct. 30, 2008

(65) Prior Publication Data

US 2010/0027750 A1 Feb. 4, 2010

(30) Foreign Application Priority Data

Nov. 2, 2007 (DE) .................. 10 2007 052 859

(51) Int. Cl.
*H05G 1/06* (2006.01)
*H05G 1/10* (2006.01)

(52) U.S. Cl. ..................................... 378/194; 378/101

(58) Field of Classification Search ......... 378/101–103, 378/119, 121, 194
See application file for complete search history.

(56) References Cited

U.S. PATENT DOCUMENTS

| 4,918,714 | A | 4/1990 | Adamski et al. ............. 378/121 |
| 2005/0254625 | A1 | 11/2005 | Schick et al. ................. 378/98 |

FOREIGN PATENT DOCUMENTS

DE 39 27 240 A1 3/1990

*Primary Examiner*—Irakli Kiknadze
(74) *Attorney, Agent, or Firm*—Fitzpatrick, Cella, Harper & Scinto

(57) ABSTRACT

The invention relates to an X-ray emitter 1 comprising an X-ray tube 2 disposed in an oil-tight housing 3 containing a high-tension transformer 2.1, wherein an electrical supply line 4 for the heater voltage for X-ray tube 2 is provided, which is led through the housing 3. Read-out and storage electronics 5 including a microcontroller 5.4 and a data storage device 5.2 are provided on or in the housing 3, and at least one period of operation of the X-ray tube 2 can be acquired and stored in the data storage device 5.2 by means of the read-out and storage electronics 5.

10 Claims, 3 Drawing Sheets

X-RAY EMITTER

TECHNICAL FIELD

The present invention relates to an X-ray emitter comprising an X-ray tube disposed in an oil-tight housing.

PRIOR ART

X-ray emitters comprise a housing, which is filled with insulating oil and which contains the X-ray tube to be connected or contacted electrically. A pre-fabricated cable feedthrough for a supply line is provided in the housing wall of the X-ray emitter for supplying power to the latter. The supply line comprises at least two electrical conductors supplying the heater voltage for the X-ray tube. The housing is designed as a so-called unitary tank which is adapted to accommodate the X-ray tube and is filled with oil. In the event of a failure of such a unitary tank, it is replaced on site and sent to the factory for reconditioning, if necessary. For failure analysis or complaint management, it is important to have information concerning the amount of usage of the X-ray emitter, e.g. the number of radiation pulses and their duration. This information can be recorded by the X-ray apparatus but is not retrievable by simple means in the factory from the specific unitary tank, since this would necessitate additional data carriers, e.g. a hardcopy or a disk. In addition, technical means for reading the data from the X-ray apparatus for the purpose of storing this information on the aforementioned data carriers would be necessary. Finally, there may also be a lack of willingness on the part of the service technician removing the unitary tank for repair purposes to cooperate in retrieving the required information on site.

It is an object of the invention to configure and arrange an X-ray emitter such that the necessary information concerning the operating time of the X-ray tube can be retrieved and stored in a simple manner.

SUMMARY OF THE INVENTION

According to the invention, read-out and storage electronics comprising a microcontroller and a data storage device are provided on or in the housing, and at least one operating time of the X-ray tube can be acquired by means of the read-out and storage electronics and stored in the data storage device. The read-out and storage electronics are disposed directly on the X-ray tube and are adapted at least to record the operating time of the X-ray tube. This information is thus available to the service technician at all times, particularly in the case of servicing or repair. The data storage device is in the form of a non-volatile data storage medium so that the stored data are retained and can be read at all times irrespective of power supply.

For this purpose, it can be advantageous to provide a high-tension transformer for the X-ray tube and an electrical supply line, passing through the housing wall, for the high-tension transformer, and to electrically couple the read-out and storage electronics to the supply line using either inductive or galvanic electrical coupling means. A constant power supply or voltage supply to the respective energy storage device would not be necessary. After each X-ray exposure and the consumption of energy stored in the energy storage device, the read-out and storage electronics are in a fully de-energized state without resulting in any loss of stored data relating to information or the program.

Additional or separate contacting of the read-out and storage electronics disposed on the X-ray emitter with the X-ray apparatus or X-ray electronics is not necessary. The read-out and storage electronics can thus be disposed on the X-ray emitter or the unitary tank, that is to say, externally on the housing of the unitary tank or in the housing itself and need only be contacted with the supply line to the X-ray emitter or X-ray tube, which is present anyway. Such contacting can be inductive or galvanic. Since contacting is performed only once at the factory, it need not be of a detachable nature. Additional externally located lines may thus be dispensed with and yet information concerning the operation of the X-ray emitter can be stored and made available from the X-ray emitter.

The read-out and storage electronics are disposed on or in the housing and can utilize the current or energy in the supply line for self-supply purposes. The read-out and storage electronics can initially be switched off and not energized in the idle state. When the primary supply voltage, or alternatively the heater voltage, is applied, the energy required for the microcontroller and data storage device can be drawn or tapped therefrom. The energy thus obtained is sufficient to record the radiation event in terms of the actual duration of radiation.

In addition to the radiation event and the duration of radiation for the creation of a radiograph, it may also be possible to record the temperature in the vicinity of the read-out and storage electronics. This temperature enables inferences to be drawn regarding the temperature in the X-ray tube. The read-out and storage electronics of the invention can be retrofitted to existing X-ray devices without much expenditure.

The duration of radiation is usually about 100 milliseconds. The radiation event, the duration of radiation, and the temperature can then be stored permanently in the non-volatile main storage device, and the energy required can be taken from energy storage device previously charged through the supply line. On completion of the storage process and following the consumption of the available energy reserve from the energy storage device, the read-out and storage electronics again assume the de-energized idle state.

Depending on the type and volume of the data storage device, at least the number of created X-ray exposures or radiation pulses and the duration and temperature thereof can in each case be stored chronologically.

In addition to the chronological storage of data, it is possible to provide for statistical storage. For this purpose, the respective radiation event can be registered in a temperature-time matrix. Read-out of the data can be performed preferably by way of an interface of the read-out and storage electronics. If the read-out and storage electronics are disposed inside the housing, the data can be read preferably inductively using RFID technology. Furthermore, it may be possible to provide additional connections for the read-out and storage electronics, for programming the read-out and storage electronics and/or for reading the data stored therein, which additional connections may be disposed inside the housing wall.

Alternatively, the read-out and storage electronics can include a separate connecting conductor for transporting energy and data, and the read-out and storage electronics can be connected to an X-ray apparatus via this connecting conductor. However, such an additional connecting conductor for the read-out and storage electronics, which conductor would not be usable for the operation of the X-ray emitter, would involve increased structural effort and thus increased expenditure.

Advantageously, the supply line can be a primary feed line for the high-tension transformer and/or a heater voltage line for the X-ray tube. The primary feed line can supply the so-called tube voltage having a potential of about 400 V. By way of inductive tapping, about 10 V to 20 V can be made available for the read-out and storage electronics within the limits of inductive energy extraction. Energy for the read-out and storage electronics is available concurrently with the tube voltage required for the X-ray exposure. The read-out and storage electronics, which may be in an inactive state at this point in time, can be activated and a rechargeable energy storage device can be charged. This activation process takes about 8 msec. The desired data, particularly the remaining duration of the X-ray exposure can then be recorded and stored by means of the read-out and storage electronics. Since the activation time is known, it can be allowed for when determining the duration of the X-ray exposure, which takes about 100 msec.

By means of inductive coupling on the primary feed line for the high-tension transformer, direct electrical contact between the read-out and storage electronics and the X-ray emitter or the control electronics can be avoided.

Furthermore, information concerning the duration of the X-ray exposure can also be acquired with the aid of such inductive tapping.

Using alternative galvanic contacting of the read-out and storage electronics with the primary feed line and/or the heater voltage line, the read-out and storage electronics may also be insulated appropriately for safety reasons, since the full supply voltage is then applied to the read-out and storage electronics.

In the case of inductive coupling on the heater voltage line, the energy for the read-out and storage electronics may already be available prior to the start of the X-ray exposure. The heater voltage power is available only when the actual X-ray exposure begins but is sufficient for activation of the read-out and storage electronics. Depending on the available energy storage device, which is charged for the duration of application of the heater voltage, the primary power need not be additionally tapped off. But in this case, it would still be necessary to tap the primary feed line for the purpose of recording the radiation event and the duration of radiation.

It may be advantageous if the read-out and storage electronics comprise a rechargeable energy storage device, which can be supplied with energy via the supply line and consists of a rechargeable battery or a capacitor. Due to electrical contacting of the read-out and storage electronics with the supply line or the heater voltage conductors, the read-out and storage electronics can be entirely dependent on the activity of the X-ray tube as regards its energy supply. Due to the use of the energy storage device, preferably a capacitor, the voltage which is applied possibly for only a few milliseconds and which is to be measured, can be used in order to obtain the energy for those evaluation and storage operations of the read-out and storage electronics that arise on activation thereof not only when the voltage is applied but also beyond that point. On completion of the radiation pulse or the X-ray exposure, the voltage can be switched off for the purpose of terminating the activity of the X-ray tube so that the read-out and storage electronics are supplied with voltage or energy beyond the actual switched-on time or operating time of the X-ray tube for the purpose of storing the desired values, i.e. the radiation event and the number of X-ray exposures, the exposure time, and the temperature.

It may also be advantageous if an inductive interface is provided, which is electrically contacted with the data storage device and by means of which the data storage device can be inductively written and/or read. The inductive interface can be connected at least to the data storage device and can preferably comprise RFID means. The inductive interface forms an inductive communications interface for a read-out device of the service technician. If the read-out and storage electronics are disposed within the housing, i.e. inside the unitary tank, the contact site between the read-out and storage electronics and the supply line can likewise be disposed in the unitary tank so that the data storage device can be read out without additional contacting through the housing wall.

Furthermore, it may be advantageous if the read-out and storage electronics have a plug contact forming an interface for feeding in or reading out data. In the external version of the read-out and storage electronics, the use of a plug contact would be a simple and cost-effective solution.

Furthermore, it may be advantageous if the read-out and storage electronics include a temperature sensor, preferably comprising an AD converter. The temperature sensor serves to record the temperature of the unitary tank in the vicinity of the read-out and storage electronics.

In this context, it may be advantageous if the read-out and storage electronics comprise a comparator circuit. The comparator circuit serves to determine the switched-on and switched-off periods for determining the exposure times of the X-ray tube from the inductively tapped voltage.

An X-ray apparatus comprising an X-ray emitter described above has the advantages provided by the invention.

BRIEF DESCRIPTION OF THE DRAWINGS

An exemplary embodiment of the invention is shown in the drawings, in which.

Figure 1:
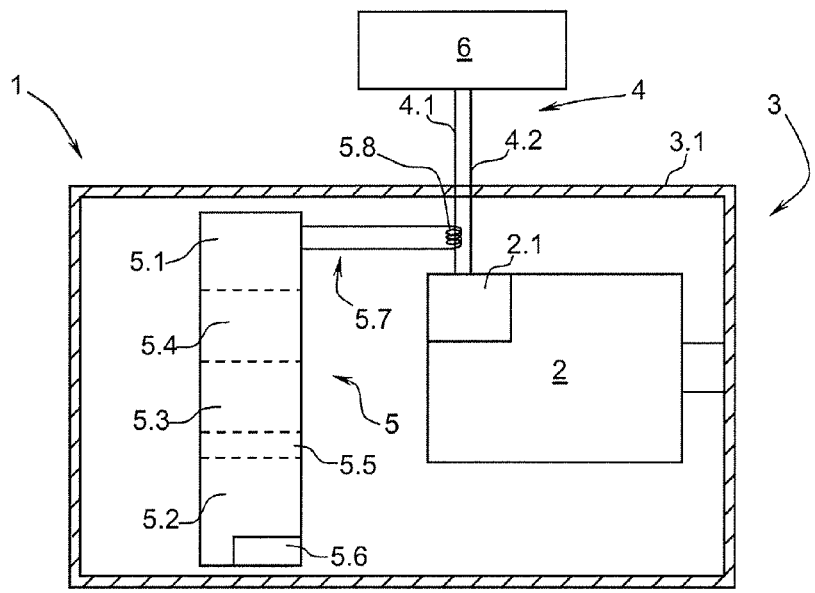
FIG. 1 is a diagram of the X-ray emitter comprising read-out and storage electronics.

An X-ray emitter 1 shown in FIG. 1 comprises a housing 3 closed on all sides by a wall 3.1. In the enclosed chamber thus formed there is disposed an X-ray tube 2 comprising a high-tension transformer 2.1, which is electrically contacted through a supply line 4. The supply line 4 comprises, inter alia, two conductors 4.1, 4.2, between which the primary supply voltage or tube voltage for the high-tension transformer 2.1 can be applied. Furthermore, the X-ray tube 2 is electrically contacted with an X-ray apparatus and X-ray apparatus electronics 6 by way of the supply line 4 and is supplied with heater voltage by the X-ray apparatus 6.

Figure 2:
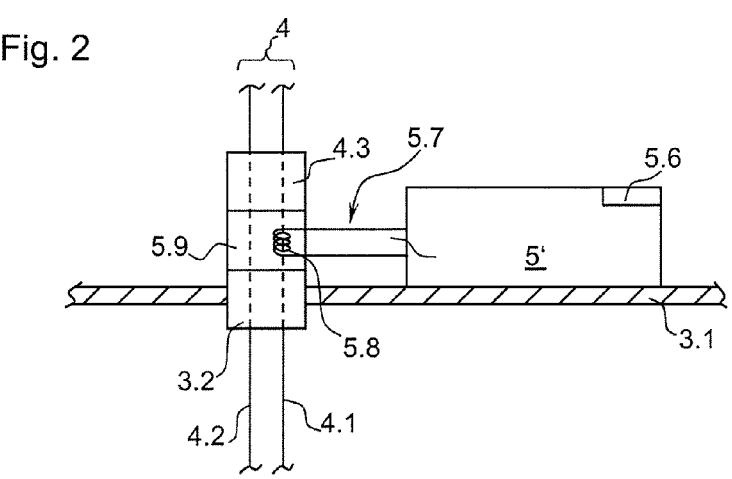
FIG. 2 is a diagram of the electrical connection comprising the contact plug.
Figure 3:
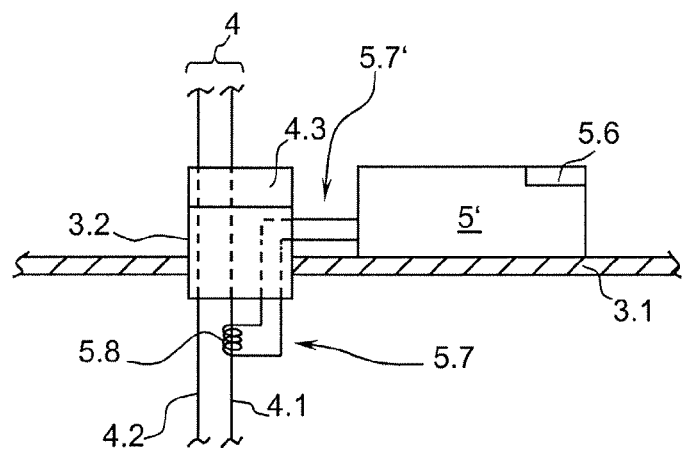
FIG. 3 is a diagram of the electrical connection comprising the feedthrough.

Furthermore, the X-ray emitter 1 comprises read-out and storage electronics 5, which are disposed inside the housing 3 designed as a unitary tank. Alternatively, the read-out and storage electronics 5 can be disposed externally on the housing 3 of the X-ray emitter 1, as shown in FIG. 2 and FIG. 3. The read-out and storage electronics 5 are inductively coupled to the supply line 4 or the primary feed line 4.1 respectively. For this purpose, the read-out and storage electronics 5 comprise an electrical connector 5.7 including a coil 5.8, through which the conductor 4.1 of the primary supply line 4 passes to execute inductive coupling.

The following description relates to the internally located read-out and storage electronics 5. The following statements likewise apply to the read-out and storage electronics 5 disposed externally on the housing 3, as shown in FIG. 2 and FIG. 3. The read-out and storage electronics 5 comprise an energy storage device 5.1 directly connected electrically to the conductors 4.1, 4.2 and adapted, when the X-ray tube 2 is switched on, to tap the potential then present at the conductors 4.1, 4.2 and store the same at least in part. The read-out and storage electronics 5 further comprise a microcontroller 5.4 and a data storage device 5.2. The data storage device 5.2 comprises an inductive interface 5.6 and is provided preferably in the vicinity of the housing wall 3.1 in order to simplify the inductive read-out of the same by means of the inductive interface 5.6. The microcontroller 5.4 serves to control data collection and evaluation, that is to say, to record the activity of the X-ray tube 2, i.e. the operating time or period of energization of the X-ray tube 2, and to store such data. A comparator circuit 5.5 is provided for the purpose of determining the operating time, i.e. the period of energization by the inductively tapped voltage.

Additionally, a temperature sensor 5.3 is provided, which is preferably equipped with an AD converter. The temperature of the read-out and storage electronics 5 at or during each radiation event is also stored via the microcontroller 5.4.

In FIG. 2, the read-out and storage electronics 5 are disposed outside the housing 3 on the housing wall 3.1. In this case, the read-out and storage electronics 5 comprise a plug contact 5.6, instead of RFID means, for feeding data to, and reading data from, the data storage device 5.2. Alternatively, RFID means 5.6 can also be used in the external version.

The housing 3 comprises a female connector 3.2, via which at least the primary voltage conductors 4.1, 4.2 can be contacted with a plug 4.3 of the supply line 4. For the purpose of inductive coupling of the externally located read-out and storage electronics 5, the electrical connector 5.7 of the read-out and storage electronics 5 comprises a contact plug 5.9. The primary voltage conductors 4.1, 4.2 are disposed inside the contact plug 5.9 for the purpose of contacting the plug 4.3 with the female connector 3.2. Furthermore, the coil 5.8, inside which the primary supply line 4.1 is led for the purpose of inductive coupling, is disposed inside the contact plug 5.9.

As shown in FIG. 3, inductive coupling takes place in the interior of the housing 3. The coil 5.8, through which the primary supply line 4.1 is led for the purpose of inductive coupling, is disposed within the housing. The electrical connecting conductor 5.7 is led through the female connector 3.2 from inside the housing toward the outside and forms the externally located connection 5.7' of the read-out and storage electronics 5 likewise disposed externally.

Figure 4:
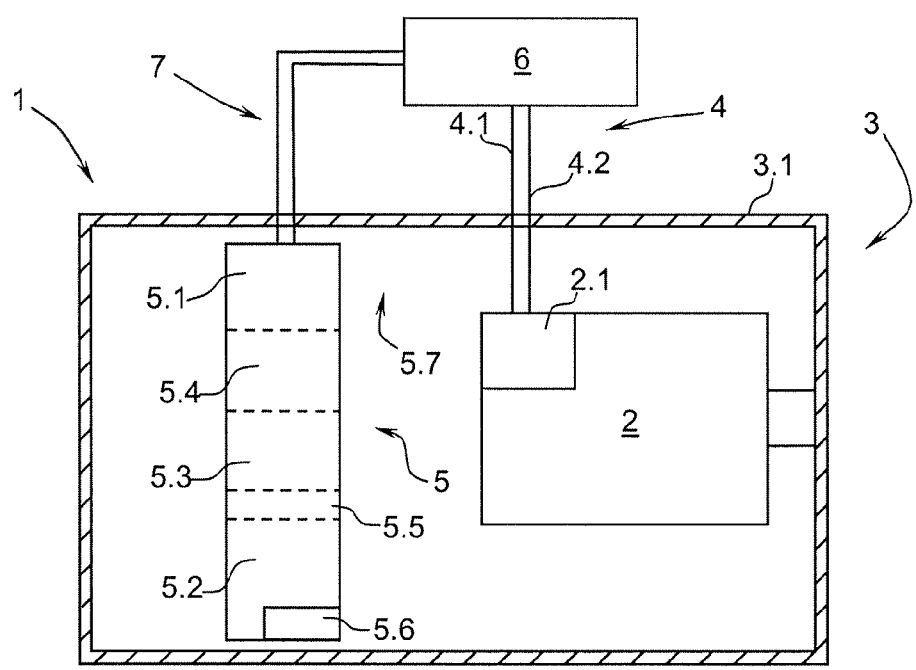
FIG. 4 is a diagram similar to FIG. 1 comprising a separate connecting conductor.

The X-ray emitter 1 shown in FIG. 4 likewise comprises read-out and storage electronics 5, which are disposed inside the housing 3 configured as a unitary tank. The read-out and storage electronics 5 are connected to the X-ray apparatus 6 by a separate connecting conductor 7. The connecting conductor 7 is also led separately through the housing wall 3.1. Similarly, a separate connecting conductor 7 leading to the X-ray apparatus 6 can also be provided for the externally located read-out and storage electronics 5 in accordance with the exemplary embodiment shown in FIG. 2 and FIG. 3.

Figure 5:
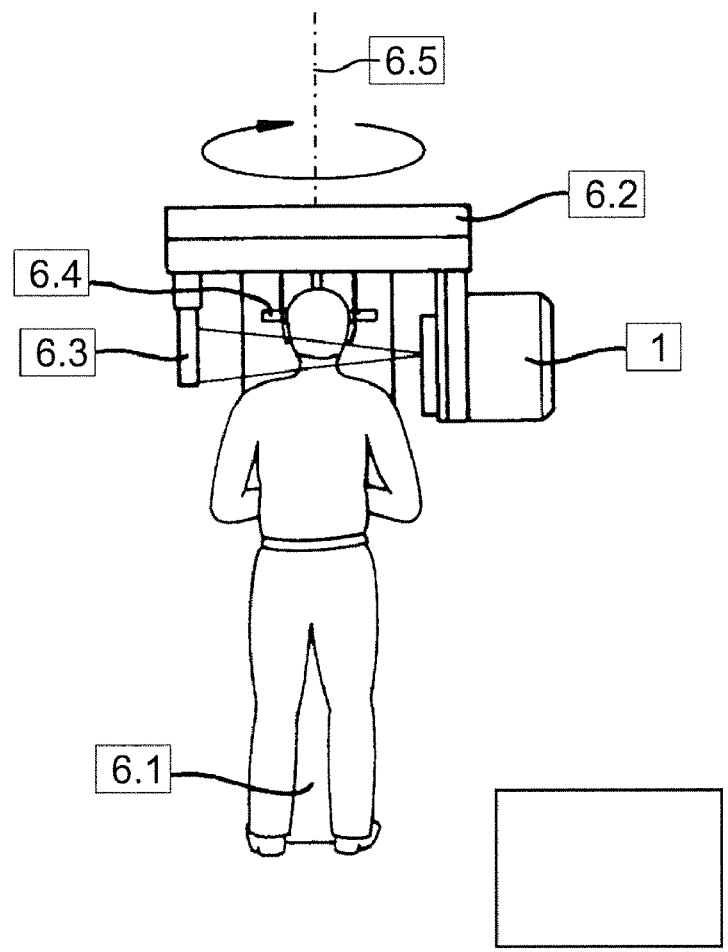
FIG. 5 shows an X-ray apparatus comprising an X-ray emitter.

The X-ray apparatus 6 shown in FIG. 5 comprises a rotary unit 6.2, which is disposed on a column 6.1 such that the rotary unit can be vertically adjusted and rotated about an axis of rotation 6.5, and on which the X-ray emitter 1, a sensor 6.3, and a head-supporting and positioning device 6.4 are disposed.

REFERENCE NUMERALS

1 X-ray emitter
2 X-ray tube
2.1 high-tension transformer
3 housing
3.1 housing wall
3.2 female connector
4 supply line
4.1 conductor, primary feed line
4.2 conductor
4.3 plug
5 read-out and storage electronics
5.1 energy storage device, battery, capacitor
5.2 data storage device
5.3 temperature sensor with AD converter
5.4 microcontroller
5.5 comparator circuit
5.6 inductive interface, RFID means, plug contact
5.7 internal electrical connector
5.7' external electrical connector
5.8 coil
5.9 contact plug
6 X-ray apparatus, X-ray electronics
6.1 column
6.2 rotary unit
6.3 sensor
6.4 head supporting and positioning device
6.5 axis of rotation
7 connecting conductor

The invention claimed is:

1. An X-ray emitter comprising:
    an X-ray tube disposed in an oil-tight housing;
    read-out and storage electronics, including a microcontroller and a data storage device, disposed on or in said housing, wherein at least one period of operation of the X-ray tube is acquired and stored in the data storage device using the read-out and storage electronics;
    a high-tension transformer for said X-ray tube; and
    an electrical supply line, led through said housing, for said high-tension transformer,
    wherein said read-out and storage electronics are electrically coupled to the supply line, and
    wherein said electrical coupling is inductive or galvanic.

2. The X-ray emitter as defined in claim 1, wherein said read-out and storage electronics include a separate connecting conductor, by means of which said read-out and storage electronics are connected to an X-ray apparatus.

3. The X-ray emitter as defined in claim 1, wherein said supply line is a primary supply line for said high-tension transformer and/or a heater voltage line for said X-ray tube.

4. The X-ray emitter as defined in claim 1, wherein said read-out and storage electronics include a chargeable energy storage device, which is supplied with voltage via said supply line.

5. The X-ray emitter as defined in claim 4, wherein said energy storage device is a rechargeable battery or a capacitor.

6. The X-ray emitter as defined in claim 1, further comprising an inductive interface, which is contacted electrically with the data storage device and via which the data storage device is inductively written to and/or read from.

7. The X-ray emitter as defined in claim 1, wherein said read-out and storage electronics include a plug contact for feeding data into, or reading data from, said data storage device.

8. The X-ray emitter as defined in claim 1, wherein said read-out and storage electronics include a temperature sensor.

9. The X-ray emitter as defined in claim 1, wherein said read-out and storage electronics include a comparator circuit.

10. An X-ray apparatus having an X-ray emitter as defined in claim 1.

* * * * *